United States Patent [19]

Werner

[11] Patent Number: 4,493,932

[45] Date of Patent: Jan. 15, 1985

[54] CHLORINE EXCHANGE FOR FLUORINE IN 2-FLUORO-PYRIDINE COMPOUNDS

[75] Inventor: John A. Werner, Antioch, Calif.

[73] Assignee: The Dow Chemical Company, Midland, Mich.

[21] Appl. No.: 417,724

[22] Filed: Sep. 13, 1982

[51] Int. Cl.[3] .................................. C07D 213/26
[52] U.S. Cl. .................................. 546/345; 546/346
[58] Field of Search ...................................... 546/345

[56] References Cited

PUBLICATIONS

Abramovitch, Pyridine and its Derivatives, Supplement Part Two, Interscience Publishers, pp. 422–423.
Morrison & Boyd, Organic Chemistry, Third Edition, pp. 1013–1016, Allyn & Bacon Pub. (1979).
Kirk–Othmer, Encyclopedia of Chemical Technology, Third Edition, vol. 12, pp. 992–995, Wiley-Interscience Pub. (1980).

*Primary Examiner*—Alan L. Rotman

[57] ABSTRACT

2-Fluoro-pyridine compounds are contacted with a chlorinating agent at superatmospheric pressures to yield 2-chloro-pyridine compounds.

9 Claims, No Drawings

CHLORINE EXCHANGE FOR FLUORINE IN 2-FLUORO-PYRIDINE COMPOUNDS

BACKGROUND OF THE INVENTION

The present invention relates to a method of exchanging chlorine atoms for fluorine atoms in 2-fluoro-pyridine compounds.

2-Chloro-5-(trifluoromethyl)pyridine compounds are commercially valuable chemical intermediates useful in the preparation of medicinal agents and agricultural chemicals. 2-Chloro-5-(trifluoromethyl)pyridine compounds are generally prepared by fluorinating a (trichloromethyl)pyridine compound.

Problems associated with the preparation of 2-chloro-5-(trifluoromethyl)pyridine compounds include (1) an over fluorinated end product, i.e., 2-fluoro-5-(trifluoromethyl)pyridines, and (2) the formation of a 2-fluoro isomer of the desired (trifluoromethyl)pyridine product generally described as a 2-fluoro-5-(chlorodifluoromethyl)pyridine compound. These 2-fluoro-pyridine by-products reduce the yield of the desired (trifluoromethyl)pyridines and necessitate additional separatory procedures which are both bothersome and expensive. The 2-fluoro isomer is a particularly annoying by-product because of the difficulty in separating it from the desired (trifluoromethyl)pyridine product.

EPO Application No. 80201077.7 (Publication No.: 0 028,870) teaches the preparation of 2-chloro-5-(trifluoromethyl)pyridine compounds employed as intermediates in the preparation of 2-pyridinyloxy(or thio)-phenoxy alkanoic acids and derivatives thereof which are herbicides. It discloses that the formation of the 2-fluoro pyridine is of no practical disadvantage since the halogen at the 2-position is displaced in the subsequent reaction with the metal salt of the hydroxy phenoxy alkanoic acid compound. Having a fluoro in the 2-pyridine ring position poses a waste stream problem with a metal fluoride (KF, NaF) when compared to a waste stream of NaCl or KCl when a chloro is in the 2-pyridine ring position. Furthermore, converting the 2-fluoro-pyridine compounds to 2-chloro pyridine compounds according to the present invention allows for the recovery of HF which can be recycled for use as a fluorinating agent. It is clearly evident that there is a need for a method of converting the 2-fluoro-pyridine by-products to the desired 2-chloro-pyridine compounds.

Heretofore, a method of displacing a fluorine atom from the 2-position of a pyridine ring with a chlorine atom has not been disclosed.

SUMMARY OF THE INVENTION

Briefly, in accordance with the present invention, a 2-fluoro-pyridine compound is reacted with a chlorinating agent at superatmospheric pressures to replace the fluorine atom in the 2-position of the pyridine ring with a chlorine atom. The chlorinated products of this method are useful as intermediates in the synthesis of biologically active compounds, such as, medicinals and herbicides.

O. particular interest in the practice of this invention is a method of replacing the fluorine atom at the 2-ring position of 3-chloro-2-fluoro-5-(trifluoromethyl)pyridine with a chlorine atom yielding 2,3-dichloro-5-(trifluoromethyl)pyridine, an intermediate in the manufacture of agricultural chemicals.

Also of interest are methods of replacing the fluorine atoms at the 2-position of 2-fluoro-5-(trifluoromethyl)pyridine; 3-chloro-2-fluoro-5-(chlorodifluoromethyl)pyridine; and 2-fluoro-5-(chlorodifluoromethyl)pyridine with a chlorine atom yielding 2-chloro-5-(trifluoromethyl)- or (chlorodifluoromethyl)-pyridine compounds.

DETAILED DESCRIPTION OF THE EMBODIMENTS

In conducting the present reaction, a 2-fluoro-pyridine compound is contacted with a chlorinating agent at a superatmospheric pressure usually in the range of from about 25 to about 400 pounds per square inch guage (psig) advantageously at a temperature in the range of from about 50° C. to about 200° C.

2-Fluoro-pyridine compounds include 3-chloro-2-fluoro-5-(trifluoromethyl)pyridine; 2-fluoro-5-(trifluoromethyl)pyridine; and the above compounds wherein -chlorodifluoromethyl or -dichlorofluoromethyl groups are substituted for the trifluoromethyl groups. The 2-fluoro-pyridine compounds can be reacted separately or as a mixture containing more than one 2-fluoro-pyridine compound.

In a preferred embodiment, a mixture containing chlorinated-(trifluoromethyl)pyridines and one or more 2-fluoro-pyridine compounds is reacted according to the present invention whereby a chlorine atom is exchanged for the fluorine atom attached to the 2-position of the pyridine ring. The above mixtures are advantageously obtained from the reaction products in the preparation of (trifluoromethyl)pyridine compounds such as, for example, 2,3-dichloro-5-(trifluoromethyl)-pyridine and 2-chloro-5-(trifluoromethyl)pyridine, whereby the 2-fluoro-pyridine compounds are undesirable by-products.

The employment of a chlorinating agent is a critical component of the present invention and HCl is suitably employed. Suitable chlorinating agents are preferably supplied in amounts to provide at least about one mole of chlorine atoms per mole of fluorine atoms to be displaced on the 2-fluoro-pyridine compounds. An excess of chlorinating agent is preferably employed and is not detrimental to the present process.

Generally, the present reaction is conducted neat or in the absence of a solvent.

In practicing the present invention, superatmospheric pressures are employed. The present reaction is conducted at a pressure of at least about 5 psig and usually at a pressure of from about 25 to about 400 psig, while 200 psig represents a preferred pressure. The upper pressure limit, i.e., 400 psig, is not meant to be a limitation of the present invention but is only set forth as an economical consideration. Conducting the present reaction at a superatmospheric pressure provides conversion of the 2-fluoro-pyridines to their corresponding 2-chloro analogs at an accelerated rate when compared to conducting the reaction at atmospheric pressure. Furthermore, the excellent yield of the desired products (about 98 percent of theoretical) avoids the use of a catalyst and provides a cleaner reaction eliminating the costs, material handling, recovery and/or disposal efforts associated with the use of catalysts.

The present reaction is advantageously conducted in the liquid phase at a temperature of between about 50° C. and about 200° C. and preferably between about 100° C. and about 125° C. A particularly preferred temperature to conduct the present reaction is about 110° C.

The present reaction is typically conducted in the presence of agitation sufficient to disperse the HCl in the liquid phase.

In conducting the present reaction, neither the rate of addition of the chlorinating agent nor the order of addition of the reactants is critical. Preferably, the suitable chlorinating agent is added in gaseous form to the 2-fluoro-pyridine compounds. A typical reaction according to the present invention generally requires from about ½ to about 24 hours to be substantially complete.

The present reaction can be characterized as follows:

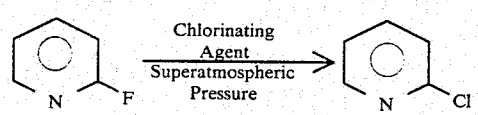

The pyridine ring may optionally contain other substituents besides the —F, such as, —Cl, —CCl₃, —CF₃, —CClF₂ and —CCl₂F. Of particular interest are reactions involving 2-fluoro-pyridine compounds which are characterized as follows:

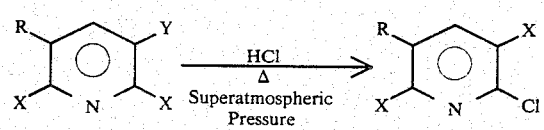

wherein

R represents —H, —CF₃, —CF₂Cl, —CCl₂F, or CCl₃; each X independently represents F, Cl or H with the proviso that at least one X is always F; and Y represents Cl or H. No attempt has been made to balance the above equations.

Especially preferred reactions, conducted at superatmospheric pressures, are characterized as follows:

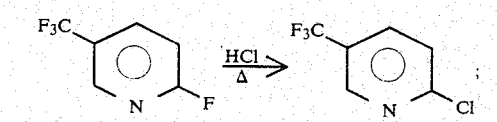

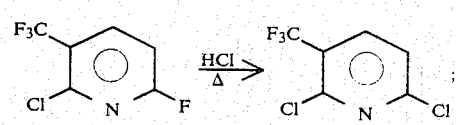

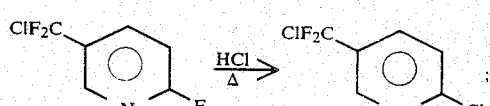

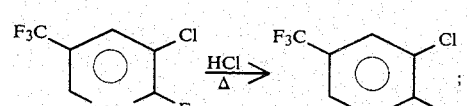

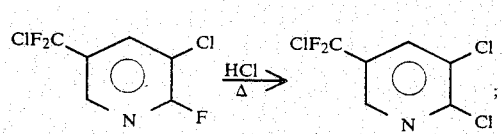

-continued

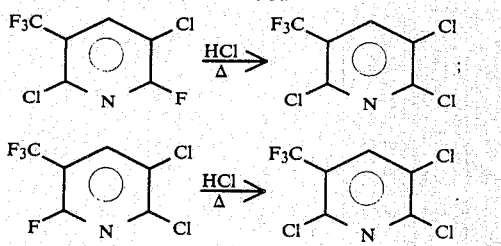

In a preferred embodiment of the present invention, the reaction product in the preparation of 2-chloro-5-(trifluoromethyl)pyridine, which contains 2-fluoro-pyridines, such as, 2-fluoro-5-(trifluoromethyl)pyridine and 2-fluoro-5-(chlorodifluoromethyl)pyridine, in addition to the desired 2-chloro-5-(trifluoromethyl)pyridine, is contacted with HCl at superatmospheric pressures and elevated temperatures as described herein to convert the 2-fluoro-pyridines to their corresponding 2-chloro analogs. The desired 2-chloro-5-(trifluoromethyl)pyridine is then readily separable from the reaction mixture by distillation since the 2-fluoro isomer, i.e. 2-fluoro-5-(chlorodifluoromethyl)pyridine, is converted to 2-chloro-5-(chlorodifluoromethyl)pyridine which has a boiling point different from the desired product.

In an especially preferred embodiment of the present invention, the reaction product in the preparation of 2,3-dichloro-5-(trifluoromethyl)pyridine, which contains 2-fluoro-pyridines, such as, 3-chloro-2-fluoro-5-(trifluoromethyl)pyridine and 3-chloro-2-fluoro-5-(chlorodifluoromethyl)pyridine, in addition to the desired 2,3-dichloro-5-(trifluoromethyl)pyridine, is contacted with HCl at superatmospheric pressures and elevated temperatures as described herein to convert the 2-fluoro-pyridines to their corresponding 2-chloro analogs. The desired 2,3-dichloro-5-(trifluoromethyl)-pyridine is then readily separable from the reaction mixture by distillation since the 2-fluoro isomer, i.e., 3-chloro-2-fluoro-5-(chlorodifluoromethyl)pyridine, is converted to 2,3-dichloro-5-(chlorodifluoromethyl)-pyridine which has a boiling point different from the desired product.

The following examples illustrate the practice of the present invention but should not be construed as limiting its scope. No attempt has been made to balance any chemical equations described herein.

EXAMPLE 1

Preparation of 2,3-Dichloro-5-(trifluoromethyl)pyridine

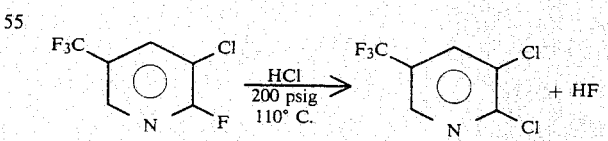

A 45 milliliter (ml) Teflon ®-lined Parr bomb, which was equipped with a pressure gauge, rupture disk and needle valve, was charged with 2 grams (g) of 3-chloro-2-fluoro-5-trifluoromethylpyridine and then pressurized with anhydrous HCl to 200 psig. The bomb was placed in a heated rocker and kept at 110° C. for 20 hours. The maximum pressure was 220 psig. The bomb was removed from the heater and allowed to cool to room temperature, at which time it was placed in an ice bath. The bomb was vented to a caustic scrubber and 2.5 g of a light tan liquid consisting of HF and 84.3% 2,3-dichloro-5-trifluoromethylpyridine (by wt.). This represents a 97.7% yield of 2,3-dichloro-5-trifluoromethylpyridine (by wt.) with 0.4% of 3-chloro-2-fluoro-5-trifluoromethylpyridine remaining. No additional products were observed by analysis with gas chromatography.

On repeating the above procedures using other substituted ring-fluorinated pyridine compounds, described herein as starting materials, substantially the same results are obtained, i.e., chloro displaces the ring-fluoro. Additionally, the present reaction is conducted as a continuous process whereby similar results are obtained.

I claim:

1. A method of exchanging a chlorine atom for a fluorine atom at the 2-position of a 2-fluoropyridine compound which comprises contacting a 2-fluoropyridine compound with an effective amount of HCL in the absence of a catalyst at a pressure of from about 5 psig to about 400 psig and an elevated temperature of from about 50° C. to about 200° C.

2. The method of claim 1 wherein said 2-fluoro-pyridine compound is a compound or a mixture of compounds of the formula

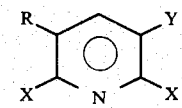

wherein
R represents —H, —CF$_3$, —CF$_2$Cl, —CFCl$_2$ or —CCl$_3$; each X independently represents F, Cl or H with the proviso that at least one X is always F; Y represents Cl or H; and with a second proviso that when each X represents F then both F in the X ring positions will be exchanged for a Cl.

3. The method of claim 2 wherein the HCl is substantially anhydrous HCl.

4. The method of claim 3 wherein said 2-fluoro-pyridine compound is 3-chloro-2-fluoro-5-(trifluoromethyl)pyridine; 3-chloro-2-fluoro-5-(chlorodifluoromethyl)pyridine; 3-chloro-2-fluoro-5-(dichlorofluoromethyl)pyridine; or mixtures thereof.

5. The method of claim 4 wherein said temperature is from about 50° C. to about 200° C. and said pressure is from about 25 to about 400 psig.

6. The method of claim 5 wherein said pressure is about 200 psig and said temperature is from about 100° C. to about 125° C.

7. The method of claim 3 wherein said 2-fluoro-pyridine compound is 2-fluoro-5-(trifluoromethyl)pyridine; 2-fluoro-5-(chlorodifluoromethyl)pyridine; 2-fluoro-5-(dichlorofluoromethyl)pyridine; or mixtures thereof.

8. The method of claim 7 wherein said temperature is from about 50° C. to about 200° C. and said pressure is from about 25 to about 400 psig.

9. The method of claim 8 wherein said pressure is about 200 psig and said temperature is from about 100° C. to about 125° C.

* * * * *